United States Patent [19]

Merkl et al.

[11] Patent Number: 5,121,628
[45] Date of Patent: Jun. 16, 1992

[54] ULTRASONIC DETECTION SYSTEM

[76] Inventors: Arthur W. Merkl, 6570 Valley Spring Crt., Birmingham, Mich. 48010; Yuji Yukishige, 3-19-19 Aogein Mino-City, Osaka, Japan

[21] Appl. No.: 594,103

[22] Filed: Oct. 9, 1990

[51] Int. Cl.$^5$ .......................... G01F 23/28; G01J 1/72; B06B 1/00
[52] U.S. Cl. .................... 73/290 V; 73/570; 73/629; 73/632; 367/908; 310/334
[58] Field of Search ............... 73/570, 584, 596, 627, 73/629, 632, 644, 290 V; 310/334; 367/119, 908

[56] References Cited

U.S. PATENT DOCUMENTS

| 4,183,007 | 1/1980 | Baird | 73/290 V X |
| 4,264,788 | 4/1981 | Keidel et al. | 310/334 |
| 4,482,835 | 11/1984 | Bar-Cohen et al. | 310/334 |
| 4,556,814 | 12/1985 | Ito et al. | 73/644 X |
| 4,576,048 | 3/1986 | Glenn | 73/629 |
| 4,594,897 | 6/1986 | Bantz | 73/644 X |
| 4,686,409 | 8/1987 | Kaarmann et al. | 73/632 X |
| 4,984,449 | 1/1991 | Caldwell et al. | 73/290 V X |

FOREIGN PATENT DOCUMENTS

| 523813 | 11/1953 | France | 73/632 |
| 796150 | 10/1954 | United Kingdom | 73/629 |
| 774675 | 5/1957 | United Kingdom | 73/629 |

Primary Examiner—William A. Cuchlinski, Jr.
Assistant Examiner—G. Bradley Bennett
Attorney, Agent, or Firm—Harness, Dickey & Pierce

[57] ABSTRACT

An ultrasonic detection system having a flat faced radiator for providing a narrow beam of ultrasonic energy with minimal dispersion. The system includes an ultrasonic transmitter and receiver unit coupled to an ultrasonic transducer for producing ultrasonic energy. The system also includes a planar radiator and a coupling device between the ultrasonic transducer and the planar radiator. An encapsulating member surrounds the ultrasonic transducer for damping ultrasonic energy transmitted by the transducer in all but one direction. The encapsulating member is also coupled to the planar radiator in areas of the planar radiator that are not coupled to the coupling means. The encapsulating member has an area of increased density immediately adjacent to the planar radiator for damping the ultrasonic energy in areas of the planar radiator that are not directly coupled to the coupling means. This results in a ultrasonic detection system that radiates a relatively narrow beam of ultrasonic energy and in which the encapsulating member is relatively decoupled from the ultrasonic energy. The flat radiating face makes the ultrasonic detection system ideally suited for applications such as level detection and particularly where the radiator must be exposed to sterilizing procedures.

16 Claims, 1 Drawing Sheet

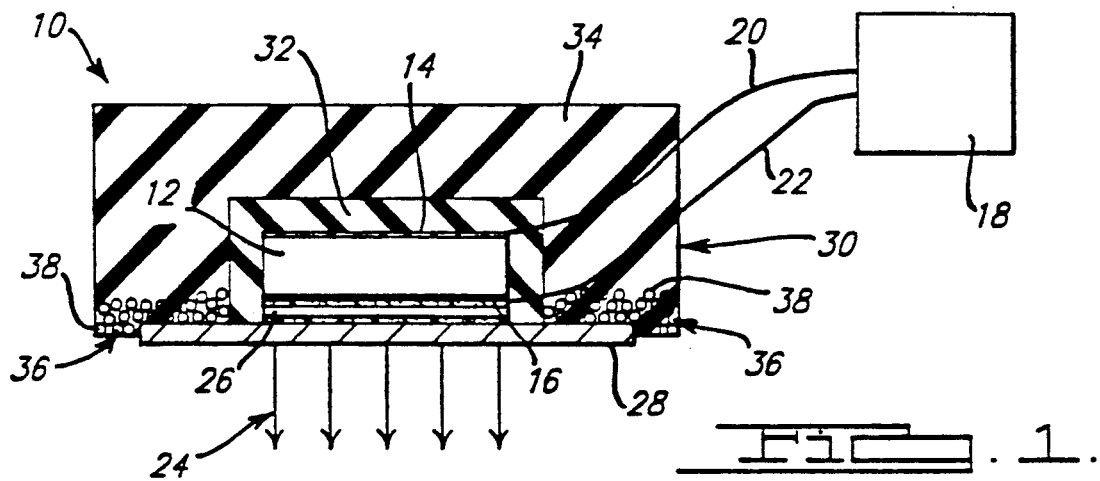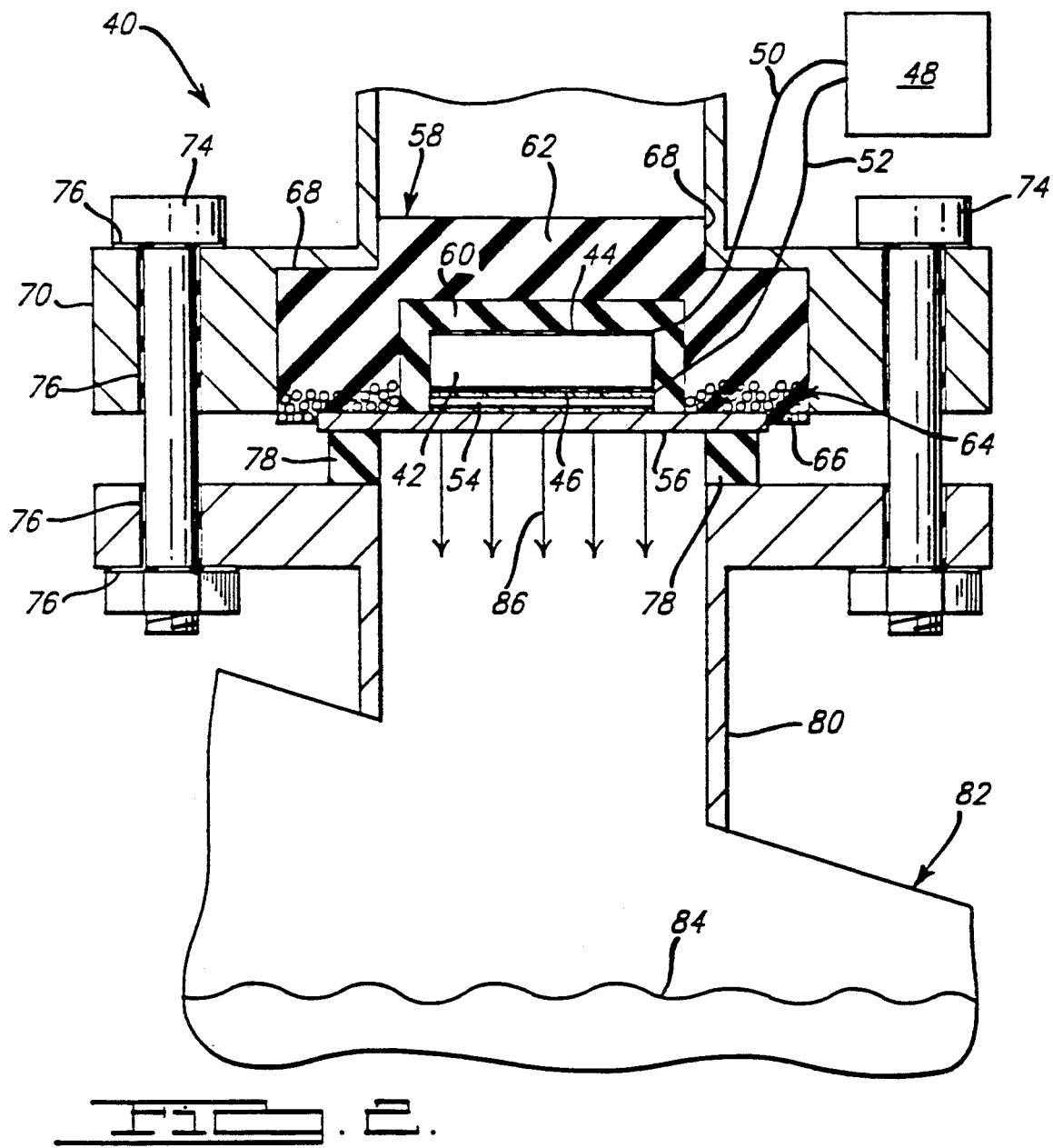

ULTRASONIC DETECTION SYSTEM

BACKGROUND OF THE INVENTION

1. Technical Field

This invention relates to ultrasonic detection systems and more particularly to an ultrasonic detector having a flat faced radiator.

2. Discussion

Ultrasonic detection systems have a wide variety of uses including object detection, range finding, level sensing, etc. In general, such systems include an ultrasonic transducer which is capable of transmitting, as well as receiving an ultrasonic beam. An ultrasonic transmitter and receiver unit may be used to transmit an electrical AC pulse at ultrasonic frequencies (15-100 KHz.) This electrical pulse causes the transducer to vibrate and thereby transmit a pulse of ultrasonic energy toward the object to be detected. When this pulse reaches the object, the pulse is reflected back to the transducer and the transducer produces an electrical pulse in response which is transmitted back to the transmitter and receiver unit. The time difference between the transmitted and received pulse, may be used to calculate the range of the object.

A number of problems arise in ultrasonic detection systems due to the spread of the ultrasonic wave before it reaches the desired object. This causes unwanted extraneous reflections back to the transducer from objects or surfaces other than the desired object. These extraneous reflections create noise in the received signal and may even completely mask the reflection from the desired object. In response, many ultrasonic detection systems include vibration absorbing damping systems in their mounting to prevent such direct transmission of ultrasonic energy. In response, many ultrasonic detection systems include a radiator for controlling the dispersion of the ultrasonic beam. For example, horn structures are frequently used to direct the path of the ultrasonic energy into a specific, defined direction. However, in a number of applications such protruding structures as horns are unacceptable because of their propensity to attract and trap debris and the difficulty in cleaning such protruding structures. For example, in ultrasonic level sensors used in sterilized environments, it is difficult or impossible to adequately clean a horn structure which is protruding into the sterilized cavity. Further, in many applications of ultrasonic detectors, space limitations preclude any protruding structure and a flat face must be used. An additional problem with prior ultrasonic detectors is that there may be a coupling of the ultrasonic energy directly from the transducer through the support structure to surrounding structures and surfaces which will also create unwanted received reflected signals. However, in many cases the isolating members add undesirable complexity, cost and bulk to the overall system.

Thus, it would be desirable to provide an ultrasonic detection system which transmits a well defined and easily controlled beam of ultrasonic energy in a single direction. It would also be desirable to provide such an ultrasonic detector which has a flat face and does not require any protruding horn or other structures to control the ultrasonic beam. Further, it would be desirable to have an ultrasonic detector which does not require complex isolating mechanisms to prevent direct production of ultrasonic energy into the surrounding mounting structure. Further, it would be desirable to provide an ultrasonic detection system with the above features which is relatively inexpensive to manufacture and simple to construct.

SUMMARY OF THE INVENTION

Pursuant to the present invention, an ultrasonic detection system is provided for directing a relatively narrow beam of ultrasonic energy from a flat faced radiator. The ultrasonic detection system includes an ultrasonic transmitter and receiver unit coupled to an ultrasonic transducer for producing ultrasonic energy. The system also includes a planar radiator having upper and lower surfaces. A coupling means is disposed between the ultrasonic transducer's flat face and the planar radiator for transferring the ultrasonic energy from the ultrasonic transducer to the planar radiator. In addition, an encapsulating member surrounds the ultrasonic transducer for dampening the ultrasonic energy transmitted by the transducer in all but one direction. The encapsulating member is also coupled to the upper surface of the planar radiator in areas of the planar radiator that are not coupled to the coupling means. Further, the encapsulating member has an area of increased density immediately adjacent to the planar radiator for damping the ultrasonic energy in areas of the planar radiator that are not directly coupled to the coupling means. In this way, the planar radiator only radiates ultrasonic energy from the area directly coupled to the coupling means. This results in a relatively narrow beam of ultrasonic energy emitted by the planar radiator in areas not dampened by the encapsulating member.

BRIEF DESCRIPTION OF THE DRAWINGS

The various advantages of the present invention will become apparent to one skilled in the art by reading the following specification and by reference to the following drawings an which:

FIG. 1 is a diagram of an ultrasonic detection system arranged in accordance with the present invention; and FIG. 2 is a diagram of a liquid level control system utilizing the ultrasonic detection system of FIG. 1.

DESCRIPTION OF THE PREFERRED EMBODIMENTS

Referring now to FIG. 1, a diagram of an ultrasonic detection system in accordance with the present invention is shown. The ultrasonic detection system 10 includes an ultrasonic transducer 12 which may comprise any means for producing ultrasonic energy in response to a signal. For example, the ultrasonic transducer 12 may be a piezoelectric transducer or a magnetostrictive transducer. The ultrasonic transducer 12 may comprise, for example, a model Piezoelectric crystal material sucha as PZT-5 manufactured by Clevite Corporation. The ultrasonic transducer has a pair of electrodes 14 and 16 attached to the upper and lower surfaces. An ultrasonic transmitter and receiver unit 18 is connected by means of conductors 20, 22 to the upper and lower electrodes 14 and 16. The transmitter and receiver unit transmits short (500 micro second) AC pulses at ultrasonic frequencies 15 KHZ-1 MHZ. This excites the ultrasonic transducer 12 to vibrate and produce an ultrasonic beam 24. In addition, the transmitter and receiver 18 is capable of receiving pulses along conductors 20,22 when returning ultrasonic waves impinge upon the ultrasonic transducer 12 causing it to produce an electrical signal. Further, the transmitter and receiver 18 also contains the necessary circuitry to analyze the time difference between the transmitted and received pulses to determine the distance of the object reflecting the return pulse. For example, one such ultrasonic transmitter and receiver unit which is suitable for use with the present invention is the model 9140 manufactured by Inventron, Inc.

It will be appreciated that when excited, the ultrasonic transducer 12 will produce ultrasonic soundwaves in many directions. To restrict the soundwaves to a single direction, the transducer is encapsulated as discussed hereinafter in accordance with the present invention. A coupling agent 26 is disposed below the bottom face of the ultrasonic transducer 12. A planar radiator 28, significantly larger than the ultrasonic transducer 12 is disposed immediately below the coupling agent 26. The coupling agent 26 is preferably bonded to the ultrasonic transducer 12 as well as to the planar radiator 28 by a suitable bonding agent such as a high temperature adhesive. This insures a direct coupling of ultrasonic energy from the transducer 12 to the coupling agent 26 and to the planar radiator 28. As a result, the planar radiator 28 will emit ultrasonic soundwaves 24 in a downward direction, as viewed in FIG. 1, when the ultrasonic transducer 12 is turned on. The planar radiator is preferably composed of stainless steel, however, other metallic or suitable non-metallic materials may also be employed. Normally, the ultrasonic transducer 12, coupling agent 26, and planar radiator will be disc or circular shaped in general, however other shapes are possible.

In order to restrict the area of ultrasonic transmission, an encapsulating container 30 is provided. The encapsulating container 30 includes an inner portion 32 which consists of a relatively uniform ultrasonic absorbing material such as silicone. The inner portion surrounds the immediate area around the ultrasonic transducer 12 and the coupling agent 26. The inner portion 32 also covers the top of the transducer 12 and a small portion of the planar radiator 28 adjacent to the edges of the coupling agent 26. The inner portion 32 may be manufactured, for example, by molding or by placing the ultrasonic transducer 12, coupling agent 26, and planar radiator 28 in a mold and molding the inner portion 32 around them.

The encapsulating container 30 also includes an outer portion 34 which extends beyond the edge of the planar radiator 28 and completely covers the inner portion 32. The outer portion 34 may be made of the same ultrasonic energy absorbing material as the inner portion 32, such as silicon. In addition, however, outer portion 34 includes an area of greater density 36 to provide selective damping of the planar radiator 28 in areas adjacent to the planar radiator 28. In accordance with a preferred embodiment, the area of greater density 36 includes a plurality of lead shot pellets 38, which may be molded into the outer portion 34 during manufacture. It will be appreciated however, that other means of increasing the damping characteristics of the outer portion 34 beside shot pellets 38 may also be advantageously employed. As a result, the planar radiator 28 will radiate ultrasonic energy that is confined to the area of the ultrasonic beam 24 directly below the ultrasonic transducer 12. Adjacent to the areas of greater density 36, ultrasonic vibration of the planar radiator 23 is effectively extinguished. Besides producing a relatively confined ultrasonic beam 24, the configuration of the present invention also facilitates mounting the ultrasonic detection system 10, since very little ultrasonic energy is transferred to the exterior of the encapsulating container 30 or the peripheral areas of the planar radiator 28. This minimizes the amount of external isolation required to isolate the ultrasonic detection system from surrounding structures.

Turning now to FIG. 2, an ultrasonic liquid level detection system 40, arranged to utilize with the present invention, is shown. The system 40 includes an ultrasonic transducer 42, upper and lower electrodes 44 and 46, an ultrasonic transmitter and receiver unit 48, a pair of electrical leads 50 and 52 connecting the transmitter and receiver to the electrodes 44, 46, as well as a coupling agent 54 and planar radiator 56 all of these components are correspondingly similar to the components described above in connection with FIG. 1.

An encapsulating container 58 surrounds the transducer 42 and planar radiator 56 and includes an inner portion 60 and an outer portion 62. The outer portion contains an area of greater density 64 which includes lead shot pellets 66 as also shown in FIG. 1. In this embodiment however, the encapsulating container 62 is adapted, by means of cutout portion 68, for engaging with a mating flange 70. Mating flange 70 is adapted to be coupled to a liquid storage tank flange 72 by means of a pair of bolts 74. Bolt isolation, while always necessary, may be provided by rubber isolation members 76. An isolating ring 78 is disposed on the liquid tank flange 72 and the planar radiator 56 rests thereupon. The liquid flange 72 is attached to a pipe extension 80 which is mounted directly to an upper portion of a liquid tank 82 containing a quantity of liquid 84.

In accordance with the embodiment shown in FIG. 2, the liquid level detection system 40 is securely affixed to the tank flange 72 in a manner which virtually eliminates direct conduction of ultrasonic energy through the apparatus into the walls of the liquid storage tank 82. When excited by the transmitter and receiver unit 48, the transducer 42 will produce an ultrasonic beam 86 which travels down the tubular extension 80 and into the interior of the liquid storage tank 82. When the ultrasonic beam reaches the surface of the liquid 84 in the tank 82, it will be reflected back up to the planar radiator 56 and conducted back to the ultrasonic transducer 42 producing a signal which is detected along lines 50, 52 by the transmitter and receiver 48. The time delay between the transmitted and received signals can be used to determine the distance from the transducer to the liquid 84 using suitable calibration techniques, this time delay can be translated to a measure of the level of the liquid 84, in the tank 82.

It will be appreciated that in some prior level measuring systems, conduction of ultrasonic energy either directly through the mounting means to the liquid storage tank 82, or alternatively from extraneous transmitted ultrasonic waves, created unwanted reflections from surfaces other than the liquid in the tank 84. In accordance with the present invention, the direction of conduction of ultrasonic energy to the liquid storage tank 82 is easily eliminated due to the decoupling achieved by the encapsulating container 30. Also the ultrasonic beam 86 is directed in a relatively narrow beam that does not disperse ultrasonic energy to the walls of the tank 82. It will be appreciated that due to the nature of the planar radiator 58, the sound energy dispersion pattern will have the characteristics of a piston radiator. That is, in general it is constrained on the edges and vibrates in the middle. This results in a dispersion pattern with most of the energy in the center and with relatively small side lobes. In contrast, other means of focusing ultrasonic beams, such as the use of a horn, radiates with moving free ends (flex mode) resulting in a sound dispersion pattern which has greater side lobes and thus greater likelihood of producing extraneous vibrations in the walls of the tank 82 Also, in the flex mode, the moving fee ends make it more difficult to damp vibrations at the ends at the edges of the transducer where the mounting is made. This would result in a mounting structure and increases the difficulty in creativity a decoupled mounting.

Further, it will be appreciated that the present invention is ideally suited for applications which require sterilization. For example, in liquid storage tanks used in the food and pharmaceutical industries frequent cleaning and sterilization is necessary. Horn type ultrasonic radiators are not practical for such applications due to their propensity to collect debris and also due to the difficulty of cleaning such debris during sterilization procedures.

In these "clean" applications, it is critical to use the material for the planar radiator 28, which is able to withstand such cleaning procedures which often involve high temperatures. Thus, metals such as stainless steel are ideally suited. Ultrasonic detection systems in which plastics radiators are used would not withstand such procedures. Further, plastic radiators are unsuitable for many applications where the liquid in the storage tank may be corrosive or may react in other ways with the plastic.

It should be noted that the encapsulating container 30 is easily molded to fit the mounting requirements of a variety of applications with minimums of isolation required.

The ultrasonic detection system 10 in accordance with the present invention can be used in a number of applications where it is desired to have a flat faced transducer in combination with narrow ultrasonic beam. These may include applications such as object detection, range finding, level detection, etc.

Those skilled in the art can appreciate that other advantages can be obtained in the use of this invention, and that modification can be made without departing from the true spirit of the invention after studying the specification, drawings and following claims.

We claim:

1. An ultrasonic detection system comprising:
   an ultrasonic transmitter and receiver unit;
   an ultrasonic transducer coupled to said ultrasonic transmitter and receiver, for producing ultrasonic energy, said ultrasonic transducer having at least one substantially planar face at its bottom surface;
   a substantially flat planar radiator member composed of a rigid material and having top and bottom planar surfaces, said radiator surfaces having a surface area larger than that of said ultrasonic transducer planar face, said planar radiator disposed below said transducer planar face and having portions extending beyond the edges of said transducer planar face;
   substantially flat planar coupling means disposed between said ultrasonic transducer planar face and said planar radiator top surface, for transferring said ultrasonic energy from said ultrasonic transducer to said planar radiator;
   an encapsulating member substantially surrounding said ultrasonic transducer for damping said ultrasonic energy transmitted by said ultrasonic transducer in all but a downward direction, said encapsulating member also being coupled to the top surface of said planar radiator in said portions of the planar radiator extending beyond the edges of said transducer planar face; and
   said encapsulating member having an area of increased density immediately adjacent to the top surface of said planar radiator extending portions for damping the ultrasonic energy in areas of said planar radiator, not directly coupled to said coupling means, wherein said planar radiator substantially radiates ultrasonic energy downward from a radiating area directly coupled to said coupling means, said radiating area having a surface area approximately equal to the surface area of said transducer planar face.

2. The ultrasonic detection system of claim 1 wherein said ultrasonic transducer is a piezoelectric transducer.

3. The ultrasonic detection system of claim 1 wherein said coupling means is coupled to both said transducer and said radiator member by means of an adhesive.

4. The ultrasonic detection system of claim 1 wherein said radiator is composed of a metallic material.

5. The ultrasonic detection system of claim 1 wherein said ultrasonic transducer, said coupling means, and said radiator are generally circular in cross-section and the diameter of said ultrasonic transducer and said coupling means are smaller than the diameter of said radiator.

6. The ultrasonic detection system of claim 1 wherein said area of increased density in said encapsulating member is separated from said ultrasonic transducer.

7. The ultrasonic detection system of claim 1 wherein said radiator produces an ultrasonic sound pressure pattern characteristic of a piston radiator.

8. The ultrasonic detection system of claim 1 further comprising means for mounting said ultrasonic transducer, encapsulating member and radiator to a liquid storage tank such that said radiator transmits ultrasonic energy vertically downward into said liquid storage tank.

9. An ultrasonic liquid level detector comprising:
   an ultrasonic transmitter and receiver unit;
   an ultrasonic transducer coupled to said ultrasonic transmitter and receiver, for producing ultrasonic energy, said ultrasonic transducer having at least one substantially planar face at its bottom surface;
   a substantially flat planar radiator member composed of a rigid material and having top and bottom planar surfaces, said radiator surfaces having a surface area larger than that of said ultrasonic transducer planar face, said planar radiator disposed below said transducer planar face and having portions extending beyond the edges of said transducer planar face;
   substantially flat planar coupling means disposed between said ultrasonic transducer planar face and said planar radiator top surface, for transferring said ultrasonic energy from said ultrasonic transducer to said planar radiator;
   an encapsulating member substantially surrounding said ultrasonic transducer for damping said ultrasonic energy transmitted by said ultrasonic transducer in all but a downward direction, said encapsulating member also being coupled to the top surface of said planar radiator in said portions of the planar radiator extending beyond the edges of said transducer planar face;

said encapsulating member having an area of increased density immediately adjacent to the top surface of said planar radiator extending portions for damping the ultrasonic energy in areas of said planar radiator not directly coupled to said coupling means, wherein said planar radiator substantially radiates ultrasonic energy downward from a radiating area directly coupled to said coupling means, said radiating area having a surface area approximately equal to the surface area of said transducer planar face; and means for mounting said ultrasonic transducer, encapsulating member and planar radiator to a liquid storage tank so that said planar radiator transmits ultrasonic energy downward into said liquid storage tank.

10. The ultrasonic detection system of claim 9 wherein said ultrasonic transducer is a piezoelectric transducer.

11. The ultrasonic detection system of claim 9 wherein said coupling means is coupled to both said transducer and said planar radiator member by means of an adhesive.

12. The ultrasonic detection system of claim 9 wherein said planar radiator is composed of a metallic material.

13. The ultrasonic detection system of claim 9 wherein said ultrasonic transducer, said coupling means, and said planar radiator are generally circular in cross-section and the diameter of said ultrasonic transducer and said coupling means are smaller that the diameter of said planar radiator.

14. The ultrasonic detection system of claim wherein said area of increased density in said encapsulating member is separated from said ultrasonic transducer.

15. The ultrasonic detection system of claim 9 wherein said planar radiator produces an ultrasonic sound pressure pattern characteristic of a piston radiator.

16. Apparatus for housing a flat-faced ultrasonic transducer having a radiator member with top and bottom planar surfaces, said radiator top surface having portions extending beyond the edge of said transducer face the apparatus comprising:

substantially flat planar coupling means disposed between a flat face of the transducer and the top surface of the radiator for transferring ultrasonic energy from the transducer to the radiator;

an encapsulating member substantially surrounding the transducer for damping the ultrasonic energy in all but a downward direction, the encapsulating member coupled to the top surface of the radiator in said portion of the radiator extending beyond the edges of said transducer planar face;

said radiator being composed of a rigid material; and the encapsulating member having an area of increased density immediately adjacent to the top surface of the radiator extending portions for damping ultrasonic energy in areas of the radiator not directly coupled to the coupling means.

* * * * *

UNITED STATES PATENT AND TRADEMARK OFFICE
CERTIFICATE OF CORRECTION

PATENT NO.    :    5,121,628                    Page 1 of 2
DATED         :    June 16, 1992
INVENTOR(S)   :    Arthur W. Merkl et al.

It is certified that error appears in the above-identified patent and that said Letters Patent is hereby corrected as shown below:

Column 2, line 38, "an" should be --in--.

Column 2, line 55, "sucha" should be --such--.

Column 3, line 51, "silicon" should be --silicone--.

Column 3, line 65, "23" should be --28--.

Column 5, line 7, after "82" insert --.--.

Column 5, line 8, "fee" should be --free--.

Column 8, line 1, Claim 13, after "smaller" insert --than--.

Column 8, line 1, Claim 13, cancel "that".

UNITED STATES PATENT AND TRADEMARK OFFICE
CERTIFICATE OF CORRECTION

PATENT NO. : 5,121,628
DATED : June 16, 1992
INVENTOR(S) : Arthur W. Merkl et al It is certified that error appears in the above-indentified patent and that said Letters Patent is hereby corrected as shown below:

Column 8, line 3, Claim 14, after "claim" insert --9--.

Signed and Sealed this

Seventh Day of December, 1993

Attest:

BRUCE LEHMAN

*Attesting Officer*  *Commissioner of Patents and Trademarks*